(12) United States Patent
Hearn

(10) Patent No.: US 8,505,548 B2
(45) Date of Patent: Aug. 13, 2013

(54) SIMULATED CIGARETTE DEVICE

(75) Inventor: Alex Hearn, London (GB)

(73) Assignee: Kind Consumer Limited, London (GB)

( * ) Notice: Subject to any disclaimer, the term of this patent is extended or adjusted under 35 U.S.C. 154(b) by 252 days.

(21) Appl. No.: 12/665,752

(22) PCT Filed: Jun. 25, 2008

(86) PCT No.: PCT/GB2008/002180
§ 371 (c)(1),
(2), (4) Date: May 28, 2010

(87) PCT Pub. No.: WO2009/001082
PCT Pub. Date: Dec. 31, 2008

(65) Prior Publication Data
US 2010/0229881 A1    Sep. 16, 2010

(30) Foreign Application Priority Data

Jun. 25, 2007 (GB) .................................. 0712304.5
Jun. 25, 2007 (GB) .................................. 0712306.0

(51) Int. Cl.
*A24F 47/00* (2006.01)

(52) U.S. Cl.
USPC ................. 131/273; 128/202.21; 128/200.14

(58) Field of Classification Search
None
See application file for complete search history.

(56) References Cited

U.S. PATENT DOCUMENTS

| | | | |
|---|---|---|---|
| 3,721,240 A * | 3/1973 | Tamburri | 128/202.21 |
| 4,393,884 A | 7/1983 | Jacobs | |
| 6,216,705 B1 | 4/2001 | Ossepian | |
| 6,889,687 B1 | 5/2005 | Olsson | |
| 2007/0119450 A1 * | 5/2007 | Wharton et al. | 128/200.23 |

FOREIGN PATENT DOCUMENTS

| | | | |
|---|---|---|---|
| CA | 2018643 A | * | 8/1991 |
| DE | 2442774 A1 | | 4/1976 |
| DE | 2653133 A1 | | 5/1978 |
| DE | 4030257 A1 | | 4/1992 |
| FR | 1601834 A | | 9/1970 |
| FR | 2654002 A | | 5/1991 |

OTHER PUBLICATIONS

International Search Report for International Application No. PCT/GB2008/002180 dated Nov. 10, 2008.
British Search Report for British Application No. 0712304.5 dated Sep. 21, 2007.
British Search Report for British Application No. 0712306.0 dated Nov. 13, 2007.

* cited by examiner

*Primary Examiner* — Richard Crispino
*Assistant Examiner* — Phu Nguyen
(74) *Attorney, Agent, or Firm* — Patterson & Sheridan, LLP

(57) ABSTRACT

A simulated cigarette device (1) comprising an elongate housing (3) having an inhaling outlet at one end (5) and a refill inlet. A reservoir (7) extends along a substantial portion of the housing and has a refill valve (6) adjacent to the refill inlet and an outlet valve (9) adjacent to the inhaling outlet, which is operable to allow gas from the reservoir to pass from the reservoir and out of the inhaling outlet. An air flow passage into the housing downstream of the reservoir leads to the inhaling outlet. A valve opening mechanism having a rotatable valve (16,28) is associated with the air flow passage and is arranged to open the outlet valve (9) as air is sucked through the air flow passage.

12 Claims, 4 Drawing Sheets

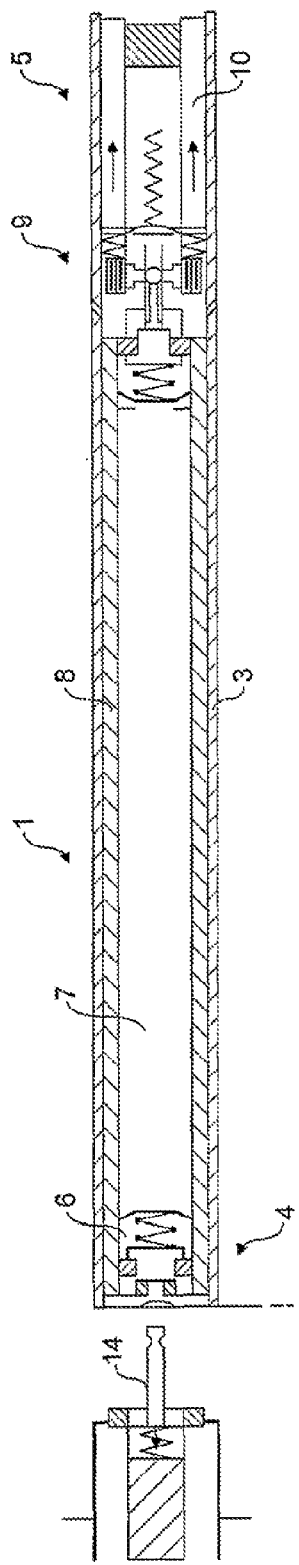
FIG. 1
FIG. 2A
FIG. 2B

SIMULATED CIGARETTE DEVICE

The present invention relates to a simulated cigarette device.

It is estimated by the World Health Organisation that tobacco smoking kills 3-4 million people per year, and that the number of smokers in the world is rising per annum. Nicotine replacements therapies have become more widespread in Western Countries but still are not having as widespread effect in making smokers quit as many had predicted. Moreover many current and ex-smokers are unsatisfied with NRT, with 67% failing to give up because they find current NRT treatments impractical, unsatisfying or uncustomary (UK Government Statistics 2004). There is a growing need for a device which replicates the same habitual patterns of smoking, which smokers are used to, as well replicating the style and functionality of a cigarette. Moreover, it is increasingly becoming apparent the need for a system which satisfies the taste and sensory needs of a smoker, a system which is able to deliver nicotine in an unmetered dosage, which a user can regulate according to his craving. One of the aims of the present invention therefore is to provide a non-carcinogenic cigarette capable of fulfilling the habitual as well as the physical cravings of smoking, which can be a socially acceptable form of nicotine replacement therapy.

With the growing restrictions on the smoking of cigarettes in public places, there is room for a device which can replace the physical act of smoking, which is socially acceptable such that it can be used in all public places. Also, there is a need for a device which can be used to dispense nicotine in a non-smokable form either as a cigarette replacement or to address the nicotine dependency that smokers feel thereby helping them to give up smoking. Other gaseous substances such as oxygen may be dispensed as these are known to have beneficial effects.

A simulated cigarette device is disclosed in U.S. Pat. No. 3,721,240. This discloses a device with a discharge valve close to the end of the device which is sucked. This valve is opened by unscrewing a cap which covers the end of the device. Gas is then discharged which can be sucked by the user. This means that gas will begin to discharge before the user sucks on the device. Further, the user may delay closing the cap or may not close the cap properly, or may forget to close the cap altogether. Under these circumstances, gas can leak from the reservoir eventually emptying the entire contents of the reservoir.

In WO 01/49349 discloses an oxygen delivery apparatus. In this case, the oxygen is displaced by the user squeezing a canister.

U.S. Pat. No. 3,631,856 discloses a simulated cigarette in which a pair of pivotal jaws provide a mechanism for opening a valve to a source of pressurised oxygen. The jaws are bitten or pressed together by hand to release the oxygen. This is an unnatural activation means for a smoker. Also, it can be activated when the user is not necessarily inhaling from the device, and could be set off accidentally when the device is not even in the user's mouth.

DE 4030257 discloses a simulated cigarette device with a breath activated valve. In this case, a circular disc is connected via an axial rod to the outlet valve for the source of materials to be inhaled. When a user sucks on the simulated cigarette, air is drawn into the device through holes upstream of the plate and is sucked around the edge of the plate thereby generating an axial force on the plate which opens the valve.

The axial valve requires a relatively high force to open and to maintain open. Because of this, the user must inhale more forcefully on the device. This does not replicate the smoking experience accurately and leads to shorter than desirable inhalation periods.

According to the present invention, there is provided a simulated cigarette device comprising an elongate housing having an inhaling outlet at one end and a refill inlet, a reservoir extending along a substantial portion of the housing and having a refill valve adjacent to the refill inlet and an outlet valve adjacent to the inhaling outlet, which is operable to allow gas from the reservoir to pass from the reservoir and out of the inhaling outlet;

further comprising an air flow passage into the housing downstream of the reservoir and leading to the inhaling outlet, and a valve opening mechanism having a rotatable valve associated with the air flow passage arranged to open the outlet valve as air is sucked through the air flow passage.

As the valve opening mechanism is arranged to open when air is sucked through the air flow passage, the user needs only to suck on the device to open the valve. No secondary action such as twisting a cap or squeezing a canister is required. This not only makes for a very simple operation, but also ensures that no gas can be dispensed until the user sucks on the device. By providing a rotatable valve, the force required to open the valve can be reduced allowing the smoking act to be replicated more closely both in terms of the force required for inhalation and the duration of the inhalation.

The rotatable valve may have a single element exposed to the airflow passage. However, preferably two or more such elements are provided in order to provide a better distribution of the air pressure on to the rotatable valve element allowing the valve to be opened more easily without excessive sucking from the user.

The or each element is preferably positioned to be not within the path of the gas from the reservoir. This prevents the element or elements from interfering with the flow of gas leading to better flow of the inhalable gas.

The valve may be closable manually, or may be closable by a user blowing into the device. However, preferably the valve is biased closed such that it closes when air stops flowing through the air flow passage.

The valve preferably has an opening, the valve being rotatable from a first position in which the opening is out of alignment with an outlet flow passage from the reservoir to the inhaling outlet such that the outlet flow passage is closed by the valve, and a second position in which the opening is aligned with the outlet flow passage to open this passage, wherein the valve opening mechanism comprises at least one vane in the air flow passage attached to the valve and being arranged to rotate the valve to the second position while air is sucked through the air flow passage. This provides a simple and reliable mechanism for allowing access to the reservoir.

There may be only a single vane. However, preferably a set of vanes is provided so that there is always at least one vane which is at or close to the optimal position in the air flow passage as the valve rotates. More preferably, there is a set of vanes at each end of the valve as this increases the opening force which is applied to the valve.

Alternatively, the rotatable valve is provided by a pair of pivotally mounted plates, each of which is positioned partly within the air flow passage and partly within the inhaling outlet passage, the plates being rotatable from a first position in which they meet one another to seal the outlet flow passage to a second position in which they are separated to open the outlet flow passage, the plate being arranged to rotate to the second position to open the outlet valve as air is sucked through the air flow passage. Preferably, the plates are biased to the first position to hold the valve closed when not in use.

Preferably, the portions of the plates which are in the outlet valve passage are generally perpendicular to the remainder of the plates. Preferably, the edges of the plates which meet one another in the closed position are resilient to ensure a good seal.

The reservoir preferably has a volume of between 500 and 10,000 mm$^3$, and more preferably between 2200 and 2600 mm$^3$. A standard pressurized solution containing nicotine, solvent, propellant and oxygen is preferably at a pressure of 2-150 bar, more preferably at 5-20 bar and optimally at 6 bar. A solution containing a high percentage of oxygen is preferably at a pressure of between 5 and 150 bar and is more preferably at a pressure of between 20 to 25 bar.

The device can typically provide between 8 and 24 puffs, most typically 12-14 puffs before the reservoir requires refilling.

The composition preferably comprises oxygen, nicotine or a derivative or salt thereof, an antioxidant, an aroma and/or flavour component, a propellant and a solvent. It may also comprise a cognitive enhancing additive. Details of the composition are given in co-pending application GB 0712308.6

A refill unit for the device forms the subject of co-pending application GB 0712305.2

An example of a device and system in accordance with the present invention will now be described with reference to the accompanying drawings, in which:

FIG. 1 is a schematic cross-section through the device also showing the refill nozzle;

FIG. 2A is a schematic cross-section through a distal end of the device with a refill valve in the closed position;

FIG. 2B is a view similar to FIG. 2a with the valve in the open position;

Figure 4:
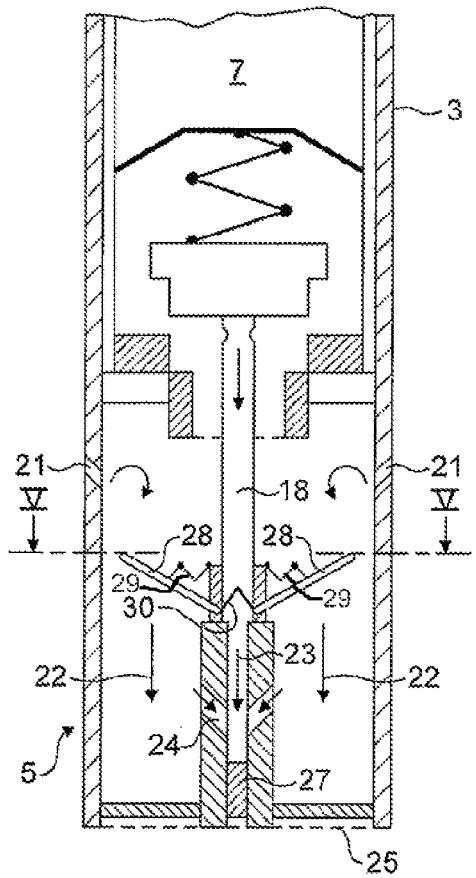
FIG. 4 is a view similar to FIG. 3 showing an alternative design of the breath activated valve.
Figure 5:
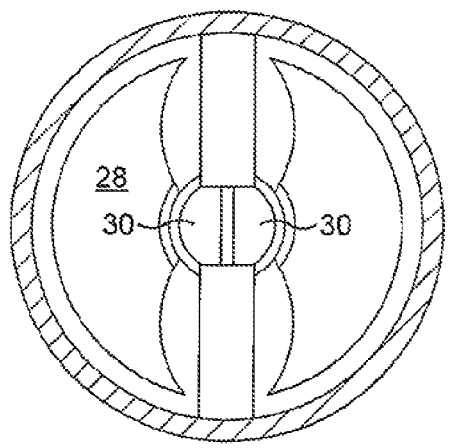
FIG. 5 is a cross-section through line V-V in FIG. 4.
Figure 6:
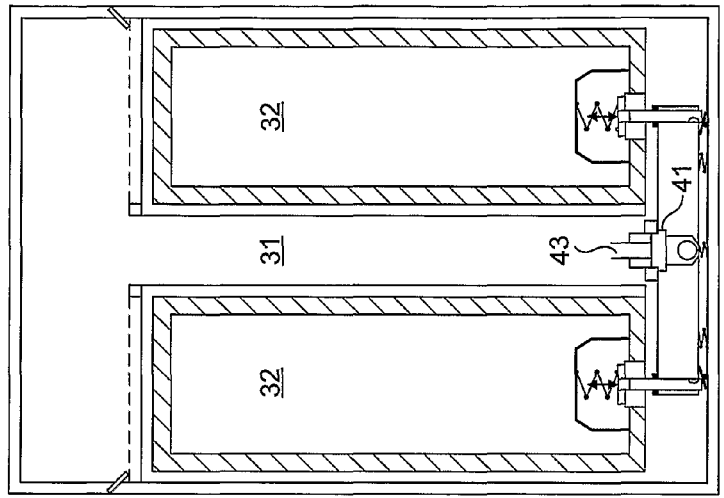
FIG. 6 is a schematic cross-section of a refill unit.
Figure 7:
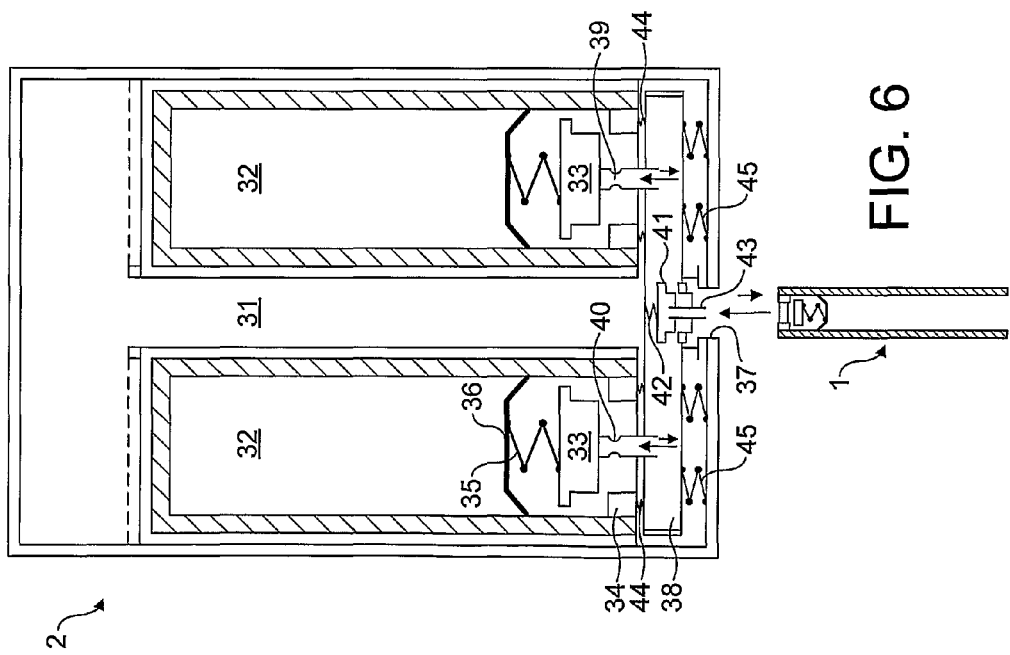
FIG. 7 is a schematic view similar to FIG. 6 of a second refill unit.
Figure 8:
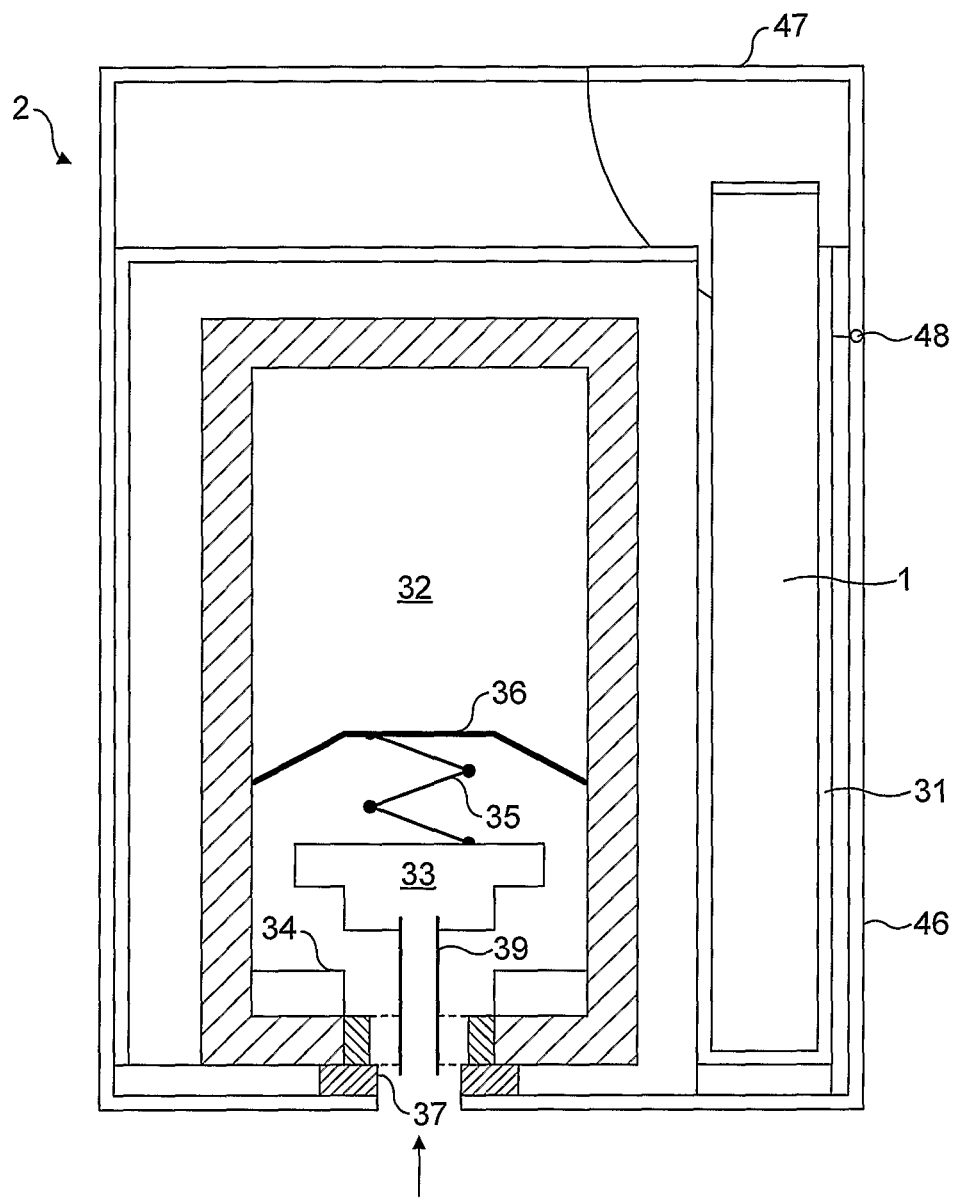
FIG. 8 is a schematic cross-section showing a third refill unit.

The system comprises two main components namely a simulated cigarette device 1 shown in FIGS. 1 to 5 and a refill unit 2 shown in FIGS. 6 to 8.

The simulated cigarette device 1 will be described first. This comprises an elongate hollow cylindrical housing 3. One end of this housing is a refill end 4 and the opposite end is an inhaling end 5. At the refill end a check valve 6 is described in more detail below. This leads to a reservoir 7 which extends along a substantial portion of the length of the device. As shown in FIG. 1, the reservoir is defined by a cylindrical sleeve 8 tightly fitted within the cylindrical housing 3. It could, however, be defined by the cylindrical housing 3 itself. At the opposite end of the reservoir 7 to the refill end 4 some three quarters of the way along the device is a breath activated outlet valve 9 that is described in more detail below. This leads to an outlet at the inhaling end 5. The reservoir 7 is periodically filled with gas through the check valve 6. A user then sucks on the inhaling end 5 periodically opening the breath activated valve 9 to draw doses of the gas from the reservoir 7.

The check valve 6 will now be described in more detail with reference to FIGS. 2A and 2B. The check valve comprises a valve element 11 which is biased onto a valve seat 12 by a spring 13. The spring 13 is supported at its opposite end by a spring support 50 which is open to allow gas to pass. The refill end 4 also has a refill seat 15 upstream of the valve element 11. In order to refill the reservoir, a refill nozzle 14 is inserted into the refill end 4 of the device 1. The refill nozzle 14 pushes on valve 11 to lift it from its seat, while the end of the nozzle seals against nozzle seat 15 to seal the end of the reservoir during the refill processes. As shown in FIG. 1, the refill nozzle 14 is spring-loaded such that it automatically dispenses gas when pressed against the valve element 11. Alternatively, an independent gas release mechanism may be provided for the refill.

As the nozzle is withdrawn, the spring 13 pushes the valve element back onto its seat to seal the end of the reservoir.

The breath activated valve 9 will now be described with reference to FIG. 3. This comprises a valve element 16 in the form of an elongate rod with a through hole 17. This through hole 17 is positioned in a tubular outlet 18 leading to the reservoir 7. In the position shown in FIG. 3, the through hole 17 is perpendicular to the tubular outlet 18 thereby blocking flow through the tubular outlet 18. When the valve element 16 is rotated through 90° the through hole 17 comes into alignment with the tubular outlet 18 allowing flow from the reservoir 7.

Figure 3:
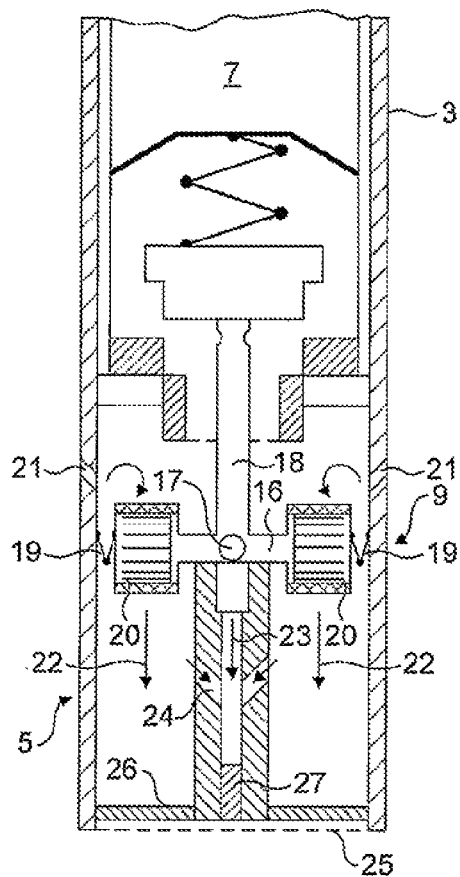
FIG. 3 is a schematic cross-section showing the breath activated valve at the proximal end.

The valve element 16 is held in the closed position shown in FIG. 3 by a pair of biasing springs 19. At either end of the valve element 16 is a vane system 20. Upstream of the vane system 20 are a pair of oblique inlets 21. These are positioned and oriented such that air flowing through the inlet impinges on the vane system 20 in such a way as to cause the valve element to rotate to the open position against the action of the biasing springs 19, thereby opening the valve. Thus, the valve is activated by a user sucking on the inhaling end of the device. When the sucking stops, the biasing springs 19 cause the valve to close.

As can be seen in FIG. 3, there are two streams flowing towards the inhaling end 5. These are the ambient air stream from the oblique inlets 21 designated by arrows 22 and the stream from the reservoir 7 which has passed through through hole 17 as designated by reference numeral 23, a pair of bleed flow orifices 24 bleed a proportion of the ambient air stream 22 into the stream 23 and are directed obliquely so as to promote flow towards the inhaling end 5. This is done as the gas from the reservoir may be particularly cold and it is therefore diluted by the ambient air from streams 20. At the inhaling end is a screen 25 which holds in place an annular filter element 26 for the external flow passageway and a central filter element 27 for the flow from the reservoir. These prevent external debris from entering the device.

An alternative arrangement of breath activated valve will now be described with reference to FIGS. 4 and 5.

Most components of the inhaling end 5 are the same as those described previously and have been designated with the same reference numerals. Only the valve mechanism itself is different. This comprises a pair of plates 28 which are pivotally mounted and biased into the first position shown in FIG. 4 by a respective balancing spring 29. Extending generally perpendicular from each plate 28 are sealing elements 30. The sealing elements 30 are preferably made of a material with a degree of resilience such as an elastomer, or may be a rigid material with a resilient tip at the end to provide a seal. The seal element meets in the middle of the tubular outlet 18 to seal the flow path through the outlet. In the device, air from oblique inlets 21 impinges on plates 28 causing the plates to rotate downwardly from the position shown in FIG. 4 thereby parting the sealing elements 30 and allowing flow from the reservoir 7. When the suction stops, the plates 28 are urged back to the starting position shown in FIG. 4 and the tubular outlet 18 is sealed again.

A first example of the refill unit will now be described with reference to FIG. 6.

The refill unit is approximately the same size as a cigarette packet and is provided a recess 31 in which the cigarette device 1 can be stored when not in use. The refill unit comprises a pair of gas cylinders 32 positioned on either side of the recess 31.

Each cylinder 32 has the same construction. Each cylinder has an inlet/outlet valve comprising a valve element 33 which is biased onto a valve seat 34 by biasing spring 35 which is supported on spring support 36.

In order to fill the cigarette device 1 from the refill unit 2, and in order to refill the refill unit 2 itself, a ducting system is provided to provide a flow communication between an inlet/outlet 37 and the cylinders 32. This takes the form of a spring-loaded duct 38 which leads from the inlet/outlet 37 to the two cylinders 32. The duct is provided with a pair of nozzles 39 each of which is arranged to press against a respective valve element 33, and each of which is provided with a plurality of orifices 40 which allow flow communication between the internal space of the cylinder 32 and the spring loaded duct 38. Adjacent to the inlet/outlet 37 is a duct valve 41 normally biased into a closed position by spring 42. A duct nozzle 43 similar to the nozzle 39 is associated with valve 41.

In an unused configuration, the spring-loaded duct 38 is biased into a position closely adjacent to the bottom of the refill unit by a spring 44. At this time, the valve elements 33 are seated as is duct valve 41, each being biased into its closed position by a respective spring. When the cigarette device 1 is inserted in the inlet/outlet 37, the check valve 6 on the cigarette device 1 is opened as described above. The duct valve 41 is pushed into an open position, and the entire spring-loaded duct 38 is lifted to the position shown in FIG. 6 assisted by springs 45. This causes nozzle 37 to lift valve elements 33 from their seats. There is now flow communication from the cylinders 32 into the reservoir 7 of the cigarette device. As the gas cylinders 32 are at the higher pressure than the cigarette device, the air flows into the reservoir 7. Each cylinder 32 is at has a sufficient gas to refill the cigarette device 14 times.

Additionally the refill unit, preferably containing an inhalable composition with oxygen, can be manually pumped by a compression pump activated by a trigger or push-down button located on the top or the side refill pack much like the manual habit associated with a cigarette lighter. This serves to prime, regulate and re-pressurize the refill unit so a constant dose and pressure is maintained and delivered.

When the cylinders 32 run low on gas, they themselves are refillable. This is done using the same mechanism as is used to refill the cigarette device from the cylinders. In order to do this, a high pressure gas source (not shown) is placed into the inlet/outlet 37 in the same way that the cigarette device is inserted and the same flow path is opened up. As the high pressure gas source is at a higher pressure than the cylinders 32, the cylinders are refilled.

It is envisaged, for example, that the high pressure gas source may be provided as a vending machine such that the user may refill their gas cylinder from this, or may be a gas canister that a user keeps in their house or car.

FIG. 7 shows a second refill unit 2. This is similar to the first unit, but, in this case, is designed to refill the cigarette device when the cigarette device is in the recess 31. Thus, the duct valve 41 and duct nozzle 43 are inverted from their positions from FIG. 6 and corresponding adjustments are made to the rest of the mechanism.

A third refill unit is shown in FIG. 8. This unit comprises a casing 46 having a lid 47 which is hinged at hinge 48. When the lid is opened, the cigarette device 1 may be inserted into and removed from recess 31. The refill comprises a single cylinder 32 constructed in accordance with the cylinders described in relation to FIG. 6. As this example only has a single cylinder, the inlet/outlet 37 directly below the nozzle 39 such that the cigarette device 1 and high pressure gas source press directly on the valve element 33.

The invention claimed is:

1. A simulated cigarette device comprising:
    an elongate housing having a main axis, an inhaling outlet at one end, and a refill inlet,
    a reservoir extending along a substantial portion of the housing and having a refill valve adjacent to the refill inlet and an outlet valve adjacent to the inhaling outlet, which is operable to allow gas from the reservoir to pass from the reservoir and out of the inhaling outlet;
    an air flow passage into the housing downstream of the reservoir and leading to the inhaling outlet, the air flow passage is open to fluid communication with the inhaling outlet when the outlet valve is closed, and
    a valve opening mechanism having a rotatable valve rotatable about an axis perpendicular to the main axis, associated with the air flow passage and arranged to open the outlet valve as air is sucked through the air flow passage.

2. A device according to claim 1, wherein the rotatable valve comprises a plurality of elements positioned to be acted on by air flowing through the air flow passage.

3. A device according to claim 2, wherein the elements are positioned such that they are not within a path of the gas from the reservoir.

4. A device according to claim 1, wherein the rotatable valve is biased closed such that it closes when air stops flowing through the air flow passage.

5. A device according to claim 1, wherein the rotatable valve has an opening, the rotatable valve being rotatable from a first position in which the opening is out of alignment with an outlet flow passage from the reservoir to the inhaling outlet such that the outlet flow passage is closed by the rotatable valve, and a second position in which the opening is aligned with the outlet flow passage to open the outlet flow passage, wherein the valve opening mechanism comprises at least one vane in the air flow passage attached to the rotatable valve and being arranged to rotate the rotatable valve to the second position while air is sucked through the air flow passage.

6. A device according to claim 5, wherein a set of vanes is provided.

7. A device according to claim 5, wherein there is a set of vanes at each end of the rotatable valve.

8. A device according to claim 2, wherein the plurality of elements comprise a pair of pivotally mounted plates, each of which is positioned partly within the air flow passage and partly within an outlet flow passage, the plates being rotatable from a first position in which the plates meet one another to seal the outlet flow passage to a second position in which the plates are separated to open the outlet flow passage, the plate plates being arranged to rotate to the second position to open the outlet valve as air is sucked through the air flow passage.

9. A device according to claim 8, wherein the plates are biased to the first position to hold the rotatable valve closed when not in use.

10. A device according to claim 8, wherein portions of the plates which are in the outlet flow passage are generally perpendicular to the remainder of the plates.

11. A device according to claim 8, wherein edges of the plates which meet one another in the first position are resilient to ensure a good seal.

12. A simulated cigarette device comprising:
an elongate housing having an inhaling outlet at one end and a refill inlet;
a reservoir extending along a substantial portion of the housing and having a refill valve adjacent to the refill inlet and an outlet valve adjacent to the inhaling outlet, which is operable to allow gas from the reservoir to pass from the reservoir and out of the inhaling outlet;
an air flow passage into the housing downstream of the reservoir and leading to the inhaling outlet; and
a valve opening mechanism having a rotatable valve associated with the air flow passage and arranged to open the outlet valve as air is sucked through the air flow passage, wherein the rotatable valve comprises a plurality of elements positioned to be acted on by air flowing through the air flow passage, wherein the plurality of elements comprise a pair of pivotally mounted plates, each of which is positioned partly within the air flow passage and partly within an outlet flow passage, the plates being rotatable from a first position in which the plates meet one another to seal the outlet flow passage to a second position in which the plates are separated to open the outlet flow passage, the plates being arranged to rotate to the second position to open the outlet valve as air is sucked through the air flow passage, wherein the plates are biased to the first position to hold the rotatable valve closed when not in use, and wherein portions of the plates which are in the outlet flow passage are generally perpendicular to the remainder of the plates.

* * * * *